(12) United States Patent
Infanger (10) Patent No.: US 9,682,196 B1
(45) Date of Patent: Jun. 20, 2017

(54) PROTECTIVE COVER FOR A SYRINGE NEEDLE

(71) Applicant: Michael Infanger, Chicago, IL (US)

(72) Inventor: Michael Infanger, Chicago, IL (US)

(73) Assignee: Verena Solutions LLC, Chicago, IL (US)

( * ) Notice: Subject to any disclaimer, the term of this patent is extended or adjusted under 35 U.S.C. 154(b) by 437 days.

(21) Appl. No.: 14/071,685

(22) Filed: Nov. 5, 2013

Related U.S. Application Data (63) Continuation-in-part of application No. 13/214,474, filed on Jan. 9, 2012, now abandoned.

(51) Int. Cl.
  *A61B 5/117* (2016.01)
  *A61M 5/32* (2006.01)
  *A61C 19/08* (2006.01)

(52) U.S. Cl.
  CPC ........... *A61M 5/3204* (2013.01); *A61C 19/08* (2013.01)

(58) Field of Classification Search
  CPC .............. A61M 5/3271; A61M 5/3273; A61M 5/3291; A61M 5/3297; A61M 5/34; A61M 5/343
  USPC .............. 433/229, 80–90; 604/263, 192–198
  See application file for complete search history.

(56) References Cited

U.S. PATENT DOCUMENTS

| | | | |
|---|---|---|---|
| 3,605,744 A | 9/1971 | Dwyer | |
| 3,820,652 A | 6/1974 | Thackston | |
| 4,425,120 A * | 1/1984 | Sampson | A61M 5/3271 604/198 |
| 4,943,282 A * | 7/1990 | Page | A61M 5/3243 604/198 |
| 4,994,045 A * | 2/1991 | Ranford | A61M 5/3271 604/198 |
| 5,137,524 A * | 8/1992 | Lynn | A61M 39/04 604/414 |
| 5,222,502 A | 6/1993 | Kurose | |
| 5,232,457 A * | 8/1993 | Grim | A61M 5/24 604/195 |
| 5,891,104 A * | 4/1999 | Shonfeld | A61M 5/3271 604/195 |
| 6,485,469 B1 * | 11/2002 | Stewart | A61M 5/3271 604/192 |
| 6,764,465 B2 * | 7/2004 | Chen | A61B 5/15003 600/577 |
| 8,721,546 B2 * | 5/2014 | Belson | A61B 5/1422 600/371 |

(Continued)

*Primary Examiner* — Yogesh Patel
(74) *Attorney, Agent, or Firm* — Andrea E. Schoen (57) ABSTRACT

A protective cover for a syringe needle includes a sheath and a needle hub. The sheath preferably includes a cylindrical body terminated with a bullet shaped end. The needle hub includes a needle base and a hypodermic needle retained in the needle base. The need base slides in the cylindrical body. The needle base includes a bullet shape and a locking projection extending from an outer perimeter of the needle base. A lengthwise slot is formed through the cylindrical body. The lengthwise slot is sized to receive a button portion of the locking projection. A retracted locking notch is formed on one end of the extension slot. An extended locking notch is formed on an opposing end of the lengthwise slot. A storage notch is formed adjacent the retracted locking notch. The button portion is retained in the retracted locking notch, the extended locking notch or the storage notch.

14 Claims, 6 Drawing Sheets

(56) References Cited

U.S. PATENT DOCUMENTS

2005/0038399 A1\* 2/2005 Suzuki ............... A61M 5/3275
604/263
2005/0245875 A1\* 11/2005 Restelli ............ A61M 25/0631
604/164.01

\* cited by examiner

PROTECTIVE COVER FOR A SYRINGE NEEDLE

CROSS-REFERENCES TO RELATED APPLICATIONS

This is a continuation-in-part application taking priority from patent application Ser. No. 13/214,474 filed on Jan. 9 2012.

BACKGROUND OF THE INVENTION

Field of the Invention

The present invention relates generally to syringes and more specifically to a protective cover for a syringe needle, which reduces the risk of injury due to accidental needle pricks.

Discussion of the Prior Art

In providing medical care for patients, anesthesia is routinely necessary. Anesthesia allows medical professionals to perform complex medical procedures, while the patient is in a sedated state allowing the medical professional more freedom to operate, and minimizing the pain felt by the patient. Anesthesia is usually administered via a non-disposable syringe, through a disposable needle.

The syringes used to administer local anesthetics use a disposable cartridge of local anesthetic and a disposable needle, which attaches to an end of the syringe. The disposable needle is supplied by the manufacturer with a two part protective cover. The back part of the cover fits over the mounting hub of the needle and extends one centimeter past a back end of the front cover and is removed when the syringe is loaded for use. The front portion remains as a protective cover to preserve the sterility of the needle and to protect a user, while handling the syringe prior to and after use. The front portion of the protective cover is referred to as a "needle cap," because of the manner in which the back portion of the cover telescopes over the front portion and the two are sealed together, an annular ridge or shoulder is created one centimeter from the back end of the front portion of the cap. All commercially available needles for dental office use at this time have a similar ridge or shoulder as the apparatus used to attach the needle to most dental syringes is the same. The needles and their protective needle caps intended for use in dental offices are supplied in different lengths for use in Mandibular and Maxillary injections. The Mandibular needle cap is 4.5 to 5 centimeters long from the previously mentioned shoulder to the front end and the Maxillary needle cap is 3 to 3.5 centimeters long between those points. The diameter of the cap at the shoulder is 1 centimeter and immediately behind the shoulder the diameter is less, usually 0.85 centimeters.

The needle cap is removed immediately prior to administering the injection to the patient. The danger of an infectious needle stick occurs when the protective needle cap is replaced on the needle, post injection, which is now contaminated with the patient's blood and saliva. A single method dominates the dental field and it includes a two handed process. The syringe is normally held in the operator's favored hand and the needle cap is held in the other. The cap and needle are then slowly brought together, until the cap has sufficiently covered the needle and locked into place at the junction of the needle and syringe. If the needle misses the opening in the cap, there is a significant chance that the hand holding the cap will be stuck and the operator exposed to any blood-borne infection carried by the patient.

To avoid this problem, the Center for Disease Control currently recommends discarding disposable syringes without replacing the needle cap. This is impractical in a dental office because only the needle, the covers, and the anesthetic capsule (or cartridge) are disposable; the remainder of the syringe is sterilized and reloaded. Often a needle is used multiple times on a single patient to administer additional anesthetic. Though the risk of an accidental stick is greater handling the uncapped syringe needle than the risk to recap the needle, needles are still reused to save time and money.

There are techniques for handling the recapping procedure to avoid the danger of a stick such as the "scooping" the cap off a table top, commonly called the 'one-handed scoop method' with the needle and pressing the cap against a wall to seat the cap on the needle base or holding the cap with a hemostat or forceps instead of the hand. These techniques work, but they are awkward at best, allow for the risk of picking up spatter, which might have fallen onto the dental tray and often ignored out of convenience. Moreover the method name is a misnomer; it in fact does require a second hand to fasten the cap securely to the needle hub once it is in place. While this method is commonly taught in dental schools, it is rarely used by tenured dentists in favor of the two-handed technique.

U.S. Pat. No. 3,605,744 to Dwyer discloses an injection apparatus and method of injection. U.S. Pat. No. 3,820,652 to Thackston discloses a packaged syringe construction. U.S. Pat. No. 5,222,502 to Ku rose discloses a blood collecting needle. U.S. Pat. No. 6,485,469 to Steward et al. discloses a shielded dental safety needle.

Accordingly, there is a clearly felt need in the art for a protective cover for a syringe needle, which reduces the risk of injury due to exposure to blood borne pathogens, because of accidental needle stick injuries incurred, while attempting to recap a syringe needle.

SUMMARY OF THE INVENTION

The present invention provides a protective cover for a syringe needle, which reduces the risk of injury due to accidental needle pricks. The protective cover for a syringe needle includes a sheath and a needle hub. The sheath preferably includes a cylindrical body, which is terminated with a hollow bullet shaped end. A needle opening is formed through a center of the hollow bullet shaped end to provide clearance for a syringe needle. The needle hub includes a needle base and a hypodermic needle. The hypodermic needle is retained in the needle base. An outer perimeter of the needle base is sized to be received by an inner perimeter of the cylindrical body and the bullet shaped end. The needle base includes a bullet shape and a locking projection extending from an outer perimeter of the needle base.

A lengthwise slot is formed through a front of the cylindrical body. The lengthwise slot extends substantially a length of said cylindrical body. The lengthwise slot is sized to receive a button portion of the locking projection. A retracted locking notch is formed on one end of the extension slot. A retracted locking finger extends into the retracted locking notch to retain the button portion of the locking projection, such that the syringe needle cannot accidentally prick a user. An extended locking notch is formed on an opposing end of the lengthwise slot. An extended locking finger extends into the extended locking notch to retain the button portion of the locking projection, such that the syringe needle may be used. A storage notch is formed on the one end of the extension slot and opposite the retracted locking notch. A storage finger extends into the storage notch to retain the locking projection of the needle base, such that the syringe needle may not be used again. A view window is preferably formed through the cylindrical body opposite the extension slot.

In use, the locking projection is snapped out of the retracted locking finger and pushed into the lengthwise slot. The button portion is slid to the other end of the lengthwise slot. The button portion is then pushed into the extended locking notch and the syringe needle is locked in an extended position by pushing the button portion into the extended locking finger. After the syringe needle has been used, the button portion is slid back into the lengthwise slot and pushed to the one end of the lengthwise projection. The locking projection is pushed into the storage notch to prevent the syringe needle from being reused.

Accordingly, it is an object of the present invention to provide a protective cover for a syringe, which reduces the risk of injury due to exposure to blood borne pathogens, because of accidental needle stick injuries incurred, while attempting to recap syringe needles.

These and additional objects, advantages, features and benefits of the present invention will become apparent from the following specification.

DETAILED DESCRIPTION OF THE PREFERRED EMBODIMENTS

Figure 1:
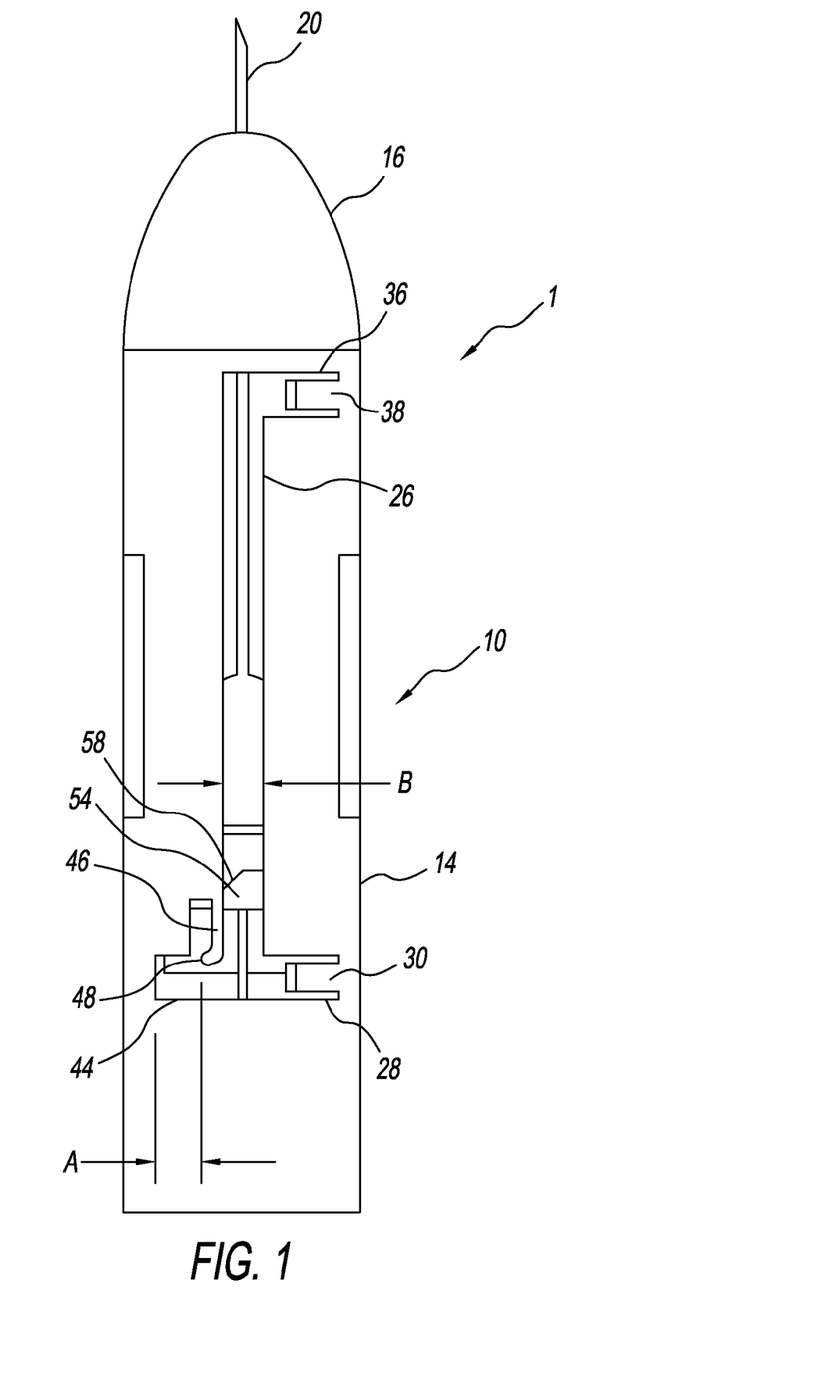
FIG. 1 is a front view of a protective cover for a syringe with a syringe needle partially extended in accordance with the present invention.
Figure 2:
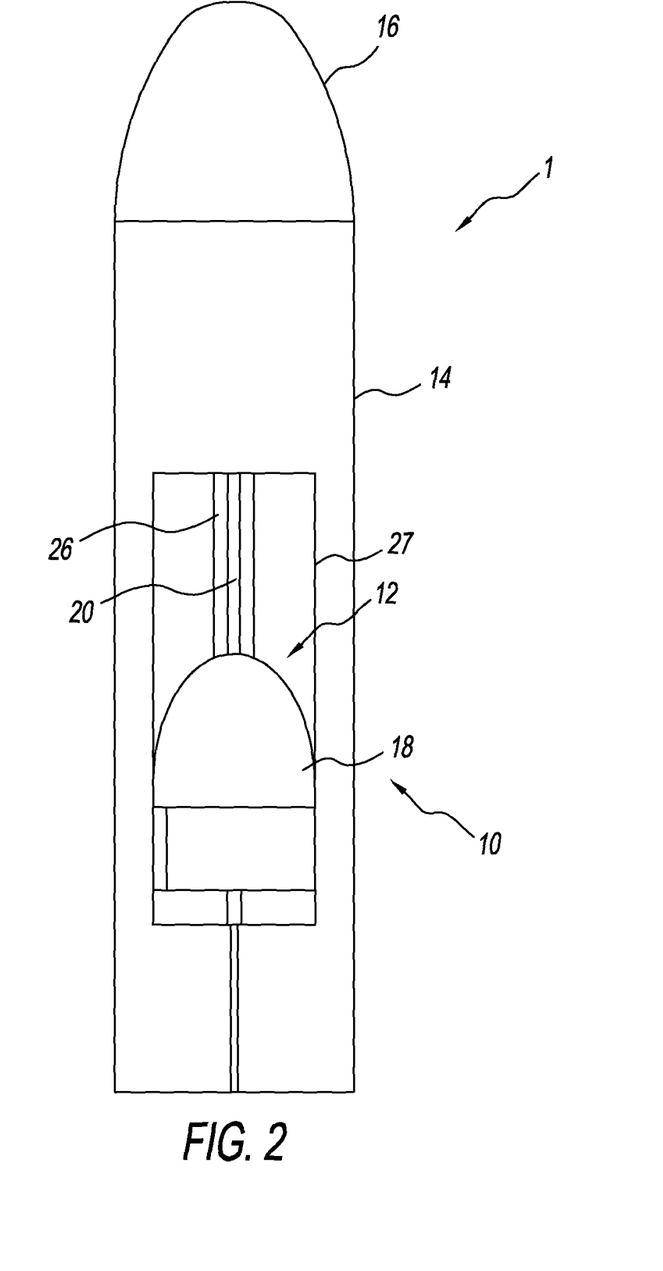
FIG. 2 is a rear view of a protective cover for a syringe with a syringe needle retracted in accordance with the present invention.
Figure 5:
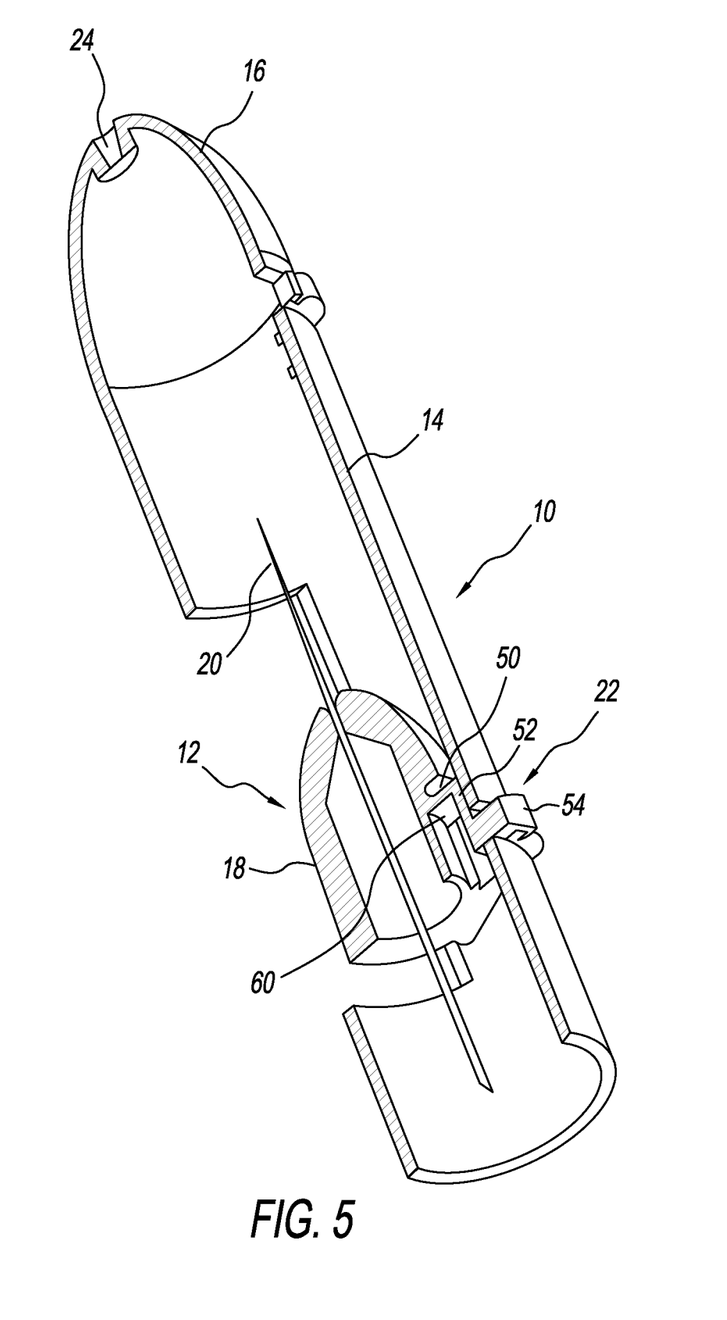
FIG. 5 is a perspective cross section view of a protective cover for a syringe needle with the syringe needle locked in a retracted position in accordance with the present invention.

With reference now to the drawings, and particularly to FIG. 1, there is shown a front view of a protective cover for a syringe needle 1. With reference to FIGS. 2 and 5, the protective cover for a syringe needle 1 includes a sheath 10 and a needle hub 12. The sheath 10 preferably includes a cylindrical body 14 and a hollow bullet shaped end 16. The cylindrical body 14 is terminated with the hollow bullet shaped end 16. The needle hub 12 includes a needle base 18, a hypodermic needle 20 and a locking projection 22. The needle base 18 has a substantial bullet shape. An outer perimeter of the needle base 18 is sized to be received by an inner perimeter of the cylindrical body 14 and the hollow bullet shaped end 16. The hypodermic needle 20 is retained in a center of the bullet shaped base 18. The locking projection 22 extends from an outer perimeter of the bullet shaped base 18. A needle opening 24 is formed through a top of the hollow bullet shaped end 16 to provide clearance for the hypodermic needle 20.

A lengthwise slot 26 is formed through a front of the cylindrical body 14. The lengthwise slot 26 extends substantially a length of the cylindrical body 14. A view window 27 is preferably formed through the cylindrical body 14 opposite the extension slot 26 to provide a visual indication of a position of the needle base 18. The lengthwise slot 26 is sized to receive a button portion 54 of the locking projection 22. A retracted locking notch 28 extends from a side of the extension slot 26 at one end thereof.

Figure 6:
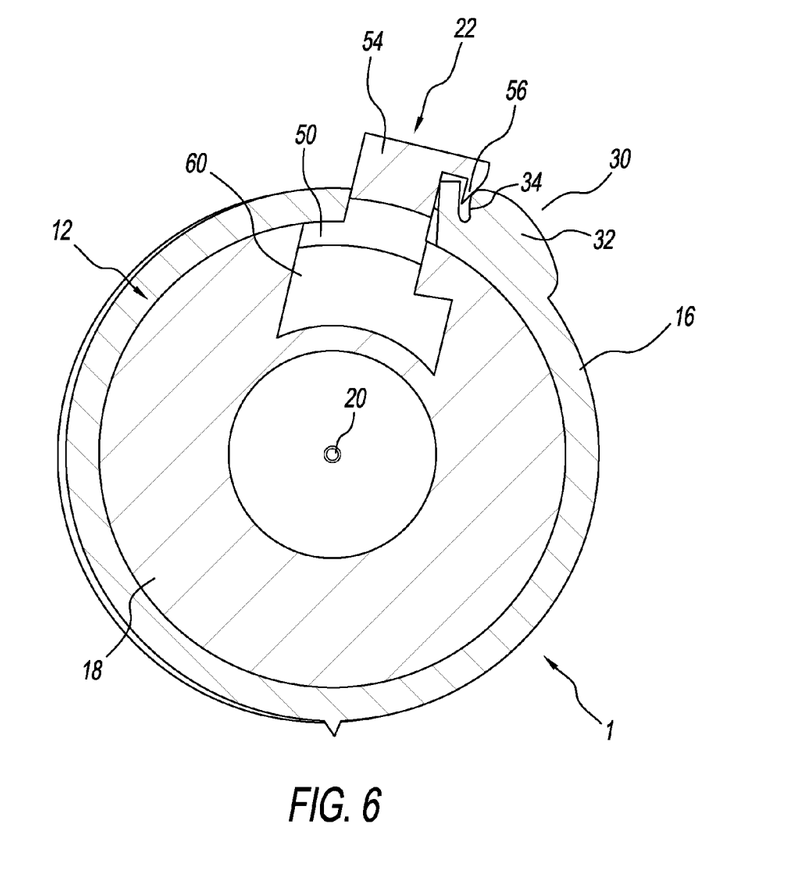
FIG. 6 is an end cross sectional view of a protective cover for a syringe needle with the syringe needle locked in a retracted position in accordance with the present invention.

With reference to FIG. 6, a retracted locking finger 30 extends into the retracted locking notch 28 to retain the button projection 54 of the locking projection 22, such that the hypodermic needle 20 cannot accidentally prick a user. The retracted locking finger 30 includes a contact portion 32 and a lock slot 34. The retracted locking finger 30 is formed as an integral portion of the cylindrical body 16. The lock slot 34 retains a locking extension 56 of the button portion 54. The contact portion 32 extends outward from a perimeter of the cylindrical body 16 to allow the retracted locking finger 30 to be depressed inward toward a center of the cylindrical body 16 to release the locking extension 56.

Figure 7:
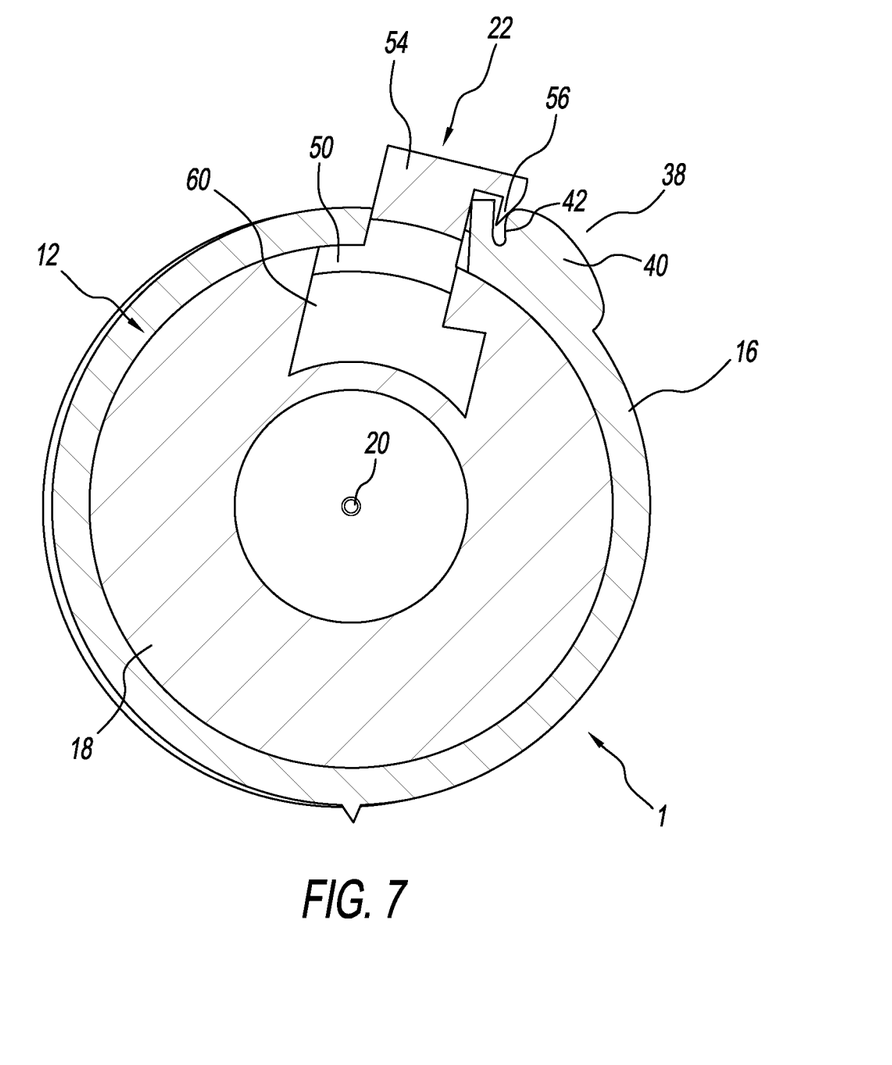
FIG. 7 is an end cross sectional view of a protective cover for a syringe needle with the syringe needle locked in an extended position in accordance with the present invention.

With reference to FIG. 7, an extended locking notch 36 extends from a side of the lengthwise slot 26 at an opposing end thereof. An extended locking finger 38 extends into the extended locking notch 36 to retain the button portion 54 of the locking projection 22, such that the hypodermic needle 20 may be used. The extended locking finger 38 includes a contact portion 40 and a lock slot 42. The extended locking finger 38 is formed as an integral portion of the cylindrical body 16. The lock slot 42 retains the locking extension 56. The contact portion 40 extends outward from a perimeter of the cylindrical body 16 to allow the extended locking finger 38 to be depressed inward toward a center of the cylindrical body 16 to release the locking extension 54.

A storage notch 44 is formed on the one end of the extension slot 26 and opposite the retracted locking notch 28. A storage finger 46 extends into the storage notch 44 to retain the locking projection 22 of the needle base 18, such that the hypodermic needle 20 may not be used again. The storage finger 46 is terminated with a lock portion 48. A distance "A" between the lock portion 48 and an end of the storage notch 44 is preferably greater than a width "B" of a button portion 54 to retain the button portion 54, such that the hypodermic needle 20 may not be used again, after the button portion has been pushed past the locking portion 48.

The locking projection 22 preferably includes a radial arm 50, an axial arm 52, the button portion 54 and the locking extension 56. The radial arm 50 extends outward from the needle base 18. The axial arm 52 extends outward from an end of the radial arm 50. The button portion 54 terminates an end of the axial arm 52. The button portion 54 is cantilevered relative to the needle base 18 through the radial arm 50 and the axial arm 52. A single cantilevered arm may used to replace the radial arm 50 and the axial arm 52. The locking extension 56 extends from the button portion 54 inward toward a center of the needle base 18. The locking extension 56 is sized to be received by the lock slots 34, 42. A chamfer 58 is formed on a side of the button portion 54 to allow the button portion 54 to be pushed past the lock portion 48. A projection cavity 60 is formed below the locking projection 22.

Figures 3, 4:
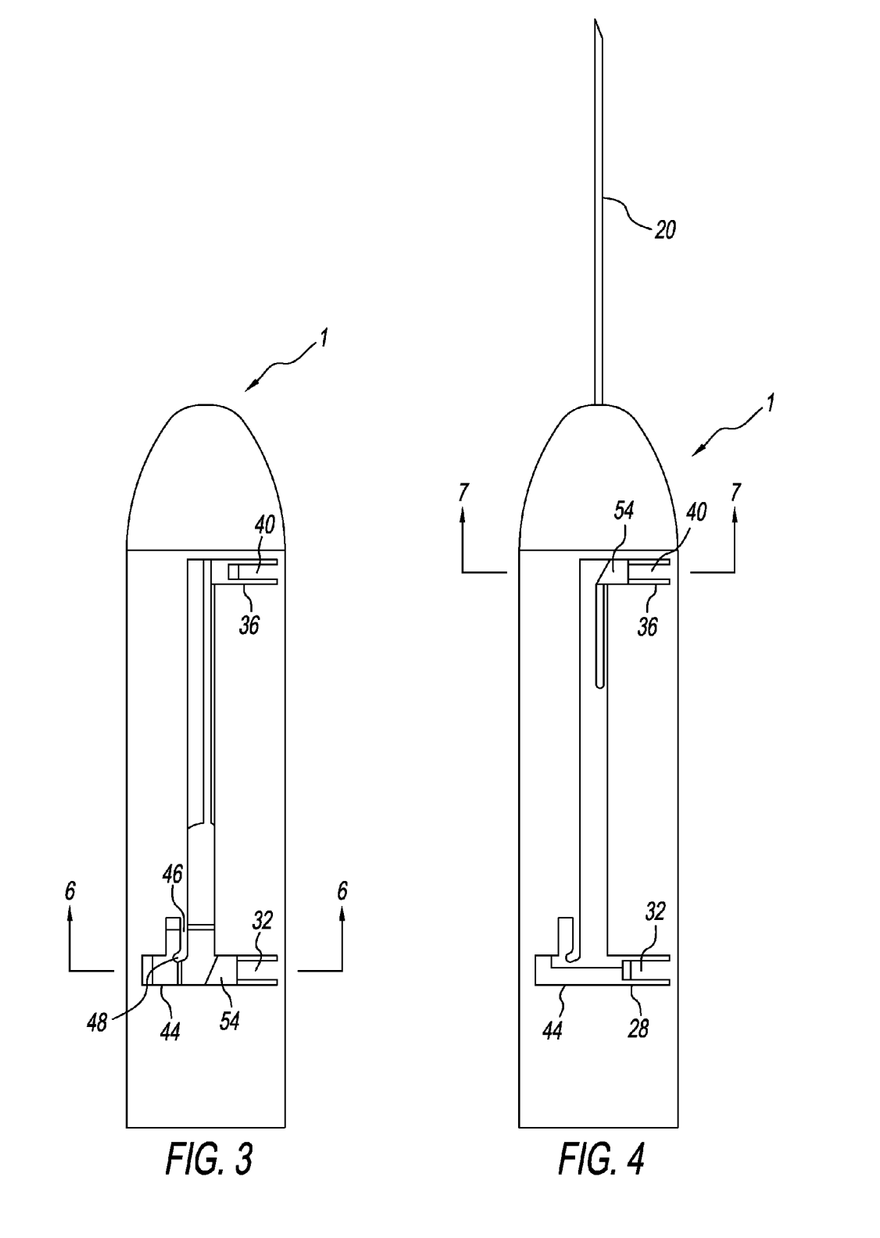
FIG. 3 is a front view of a protective cover for a syringe with the syringe needle locked in a retracted position in accordance with the present invention.
FIG. 4 is a front view of a protective cover for a syringe with the syringe needle locked in an extended position in accordance with the present invention.

With reference to FIGS. 3-4, the contact portion 32 of the retracted locking finger 30 is depressed with one hand and the button portion 54 of the locking projection 22 is slid out of the retracted locking notch 28 into the lengthwise slot 26 with the other hand. The button portion 54 of the locking projection 22 is slid to the other end of the lengthwise slot 26. The locking extension 56 of the locking projection 22 is then pushed into lock slot 42 of the extended locking finger 38 and the hypodermic needle 20 is locked in an extended position. After the hypodermic needle 20 has been used, the contact portion 40 is depressed with one hand and the button portion 54 is slid out of the extended locking notch 28 into the lengthwise slot 26 with the other hand. The button portion 54 is slid down the lengthwise slot 26 to the storage notch 44. The button portion 54 is pushed into the storage notch 44 past the lock portion 48 to prevent the hypodermic needle 20 from being reused.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A protective cover for a syringe needle comprising
(a) a sheath comprising a cylindrical body with a lengthwise slot, a retracted locking notch extending perpendicularly outward from one end of the lengthwise slot, an extended locking notch extending perpendicularly outward from the opposing end of the lengthwise slot, and a storage notch extending perpendicularly outward from the lengthwise slot and
(b) a needle hub located within the sheath comprising a needle and a needle base, wherein the needle base comprises a locking projection that extends through the lengthwise slot and that can be slid through the lengthwise slot into the retracted locking notch, the extended locking notch, or the storage notch, wherein pushing the locking projection into the storage notch locks the needle in a retracted position so that the needle cannot be used again.

2. The protective cover of claim 1, wherein sliding the locking projection through the lengthwise slot towards the extended locking notch extends the needle from the sheath and sliding the locking projection through the lengthwise slot towards the retracted locking notch retracts the needle into the sheath.

3. The protective cover of claim 1, wherein the lengthwise slot extends substantially a length of the cylindrical body.

4. The protective cover of claim 1, wherein the cylindrical body is terminated with a bullet shaped end.

5. The protective cover of claim 4, wherein a needle opening is formed through a center of the bullet shaped end.

6. The protective cover of claim 1, wherein an outer perimeter of the needle base is sized to be received by an inner perimeter of the cylindrical body.

7. The protective cover of claim 1, wherein said needle hub may be secured to a syringe.

8. The protective cover of claim 1, wherein twisting the needle hub relative to the sheath pushes the locking projection into the retracted locking notch or the extended locking notch.

9. The protective cover of claim 1, wherein pushing the locking projection into the retracted locking notch locks the needle in a retracted position and pushing the locking projection into the extended locking notch locks the needle in an extended position.

10. The protective cover of claim 1, wherein the storage notch is located opposite the retracted locking notch on the same end of the lengthwise slot as the retracted locking notch.

11. The protective cover of claim 1, wherein a view window is formed in said cylindrical body to provide a visual indication of a position of the needle hub.

12. The protective cover of claim 1, wherein the locking projection includes a cantilevered arm extending outward from the needle base, a button portion extending from an end of the cantilevered arm, and a locking extension extending from the button portion.

13. The protective cover of claim 1, wherein the sheath further comprises a retracted locking finger located in the retracted locking notch and an extended locking finger located in the extended locking notch.

14. The protective cover of claim 1, wherein the sheath further comprises a storage finger located in the storage notch.

\* \* \* \* \*